United States Patent [19]

Hess

[11] Patent Number: 4,664,120

[45] Date of Patent: May 12, 1987

[54] ADJUSTABLE ISODIAMETRIC ATRIAL-VENTRICULAR PERVENOUS LEAD

[75] Inventor: Stanley R. Hess, Miami, Fla.

[73] Assignee: Cordis Corporation, Miami, Fla.

[21] Appl. No.: 821,242

[22] Filed: Jan. 22, 1986

[51] Int. Cl.⁴ .......................... A61B 5/04; A61N 1/05
[52] U.S. Cl. ................................. 128/642; 128/785; 128/786; 128/419 P
[58] Field of Search .............................. 128/784–786, 128/419 P, 642

[56] References Cited

U.S. PATENT DOCUMENTS

| 4,402,329 | 9/1983 | Williams | 128/785 |
| 4,458,677 | 7/1984 | McCorkle, Jr. | 128/786 |
| 4,574,814 | 3/1986 | Buffet | 128/786 |

FOREIGN PATENT DOCUMENTS 2132895  7/1984  United Kingdom ................ 128/786

Primary Examiner—Lee S. Cohen
Attorney, Agent, or Firm—Lockwood, Alex, Fitzgibbon & Cummings

[57] ABSTRACT

A disposable atrial-ventricular percutaneous lead is provided which is suitable for carrying out a variety of functions, including endocardial pacing, mapping or diagnosis. The percutaneous lead maintains an isodiametric profile for insertion through a body cavity such as a vein or artery. By manipulation of a proximal end portion of the device, the length of extension of the ventricular electrode assembly can be adjusted, and a longitudinally spaced atrial electrode assembly can be radially expanded, the adjustability of these various assemblies permitting accommodation of a variety of differently sized hearts while retaining an isodiametric configuration for effective pervenous insertion. More than one atrial electrode may be incorporated in the lead to provide for bipolar stimulation and sensing of the atrium.

18 Claims, 7 Drawing Figures

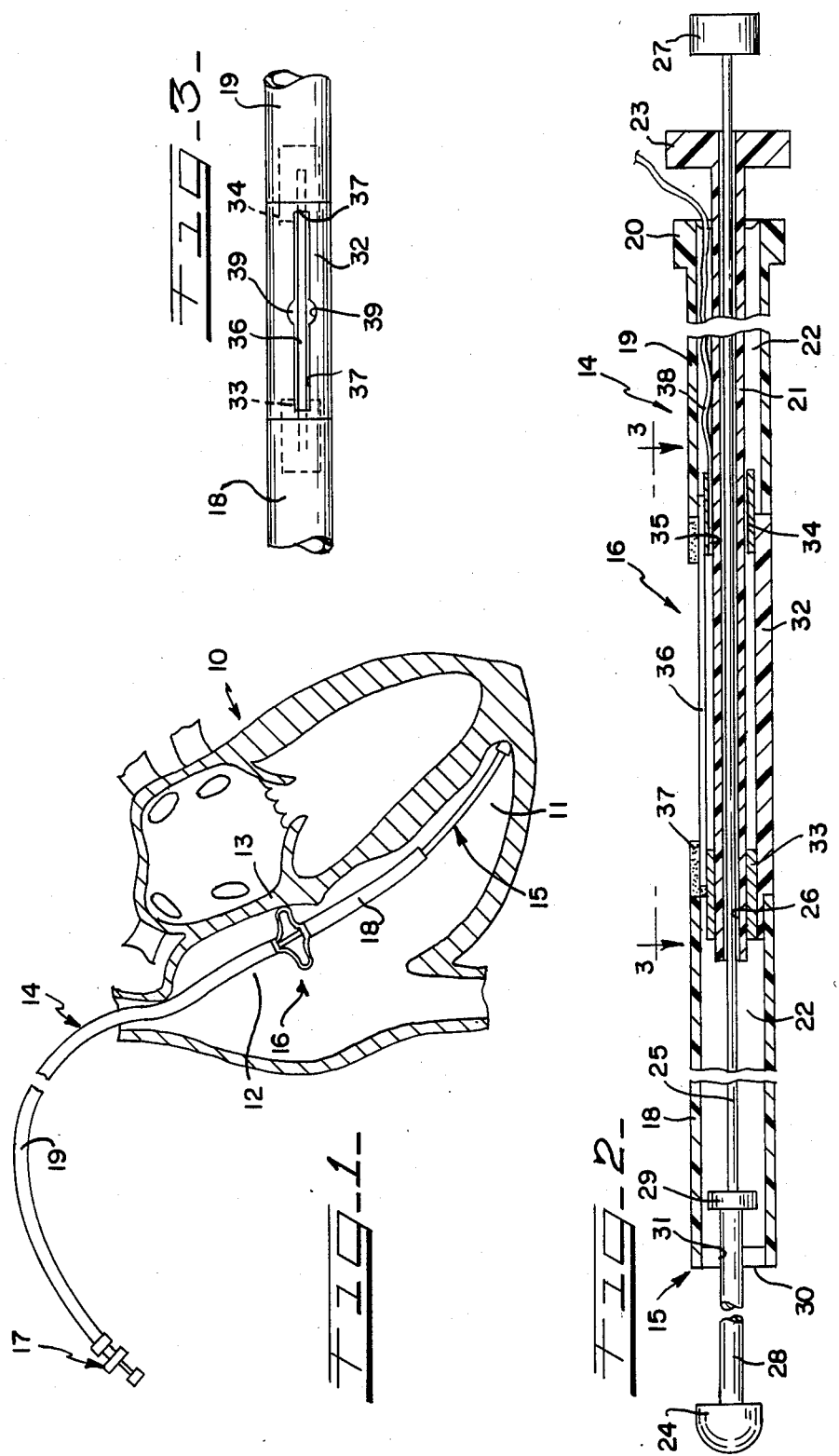

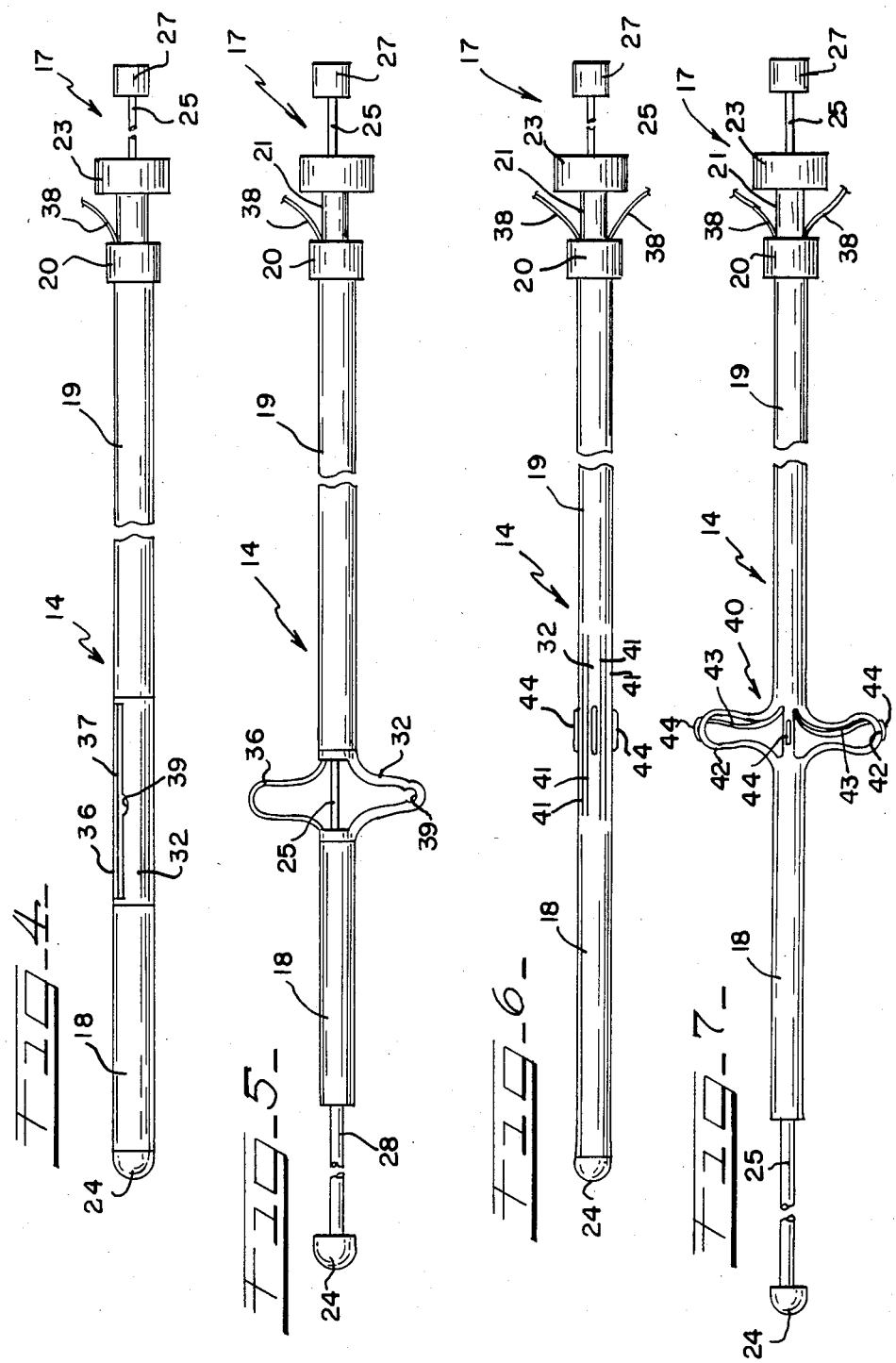

ADJUSTABLE ISODIAMETRIC ATRIAL-VENTRICULAR PERVENOUS LEAD

BACKGROUND AND DESCRIPTION OF THE INVENTION

The present invention generally relates to percutaneous leads for medical or surgical uses, such leads being capable of performing multiple functions, such as mapping or pacing, in connection with the diagnosing or treatment of cardiac conditions, the leads being particularly well suited for use as disposable, temporary treatment devices.

Electrophysiological studies and treatments of patients have in the past utilized many different devices and systems including those that incorporated an elongated percutaneous lead that provides an electrically conductive elongated pathway between a location that is external of the patient and a location within the patient at which sensing, stimulation or treatment is to take place. When this percutaneous route is taken in conjunction with studies or treatment of the heart, this is known as an endocardial approach. While an epicardial approach is possible, this is not always the most suitable procedure since it requires thoractomy and the exposure of the heart. Endocardial approaches are typically preferred because they are substantially less intrusive. Such procedures typically require accurate location of each electrode at specific locations on cardiac tissue.

The pacing function is well known in the art, whereby an electrical impulse is imparted to a particular location of the body in order to either assist proper functioning of a body organ or in order to control or bring under control an iatrogenic or spontaneous dysrhythmia by pacing a ventricle, or in order to stimulate or pace the heart so as to assist in mapping its electrical pathways. Regarding the mapping function, such is undertaken to identify specific foci or anatomical locations which, for example, are a source of abnormal cardiac rhythm in patients with dysrhythmias.

While the foregoing functions may be readily performed while following the epicardial approach involving the exposure of the heart, there is a need for a more sophisticated and thorough utilization of these functions in connection with the substantially less intrusive endocardial approach. Accordingly, there is a need for a device that has the attributes of the less intrusive endocardial approach while still providing substantial control, adjustability and feasibility for studies and treatments including those involving any or all of pacing or mapping leads.

In addition to the foregoing, when an attempt is made to carry out multiple testing and/or treating functions of the type described using the endocardial approach, the use of two temporary pervenous leads is often required. One lead is needed for the ventricle and the other is needed for the atrium, and the introduction of the second lead in the same vein or in a second access site can dislodge the first lead from its position in the chamber of choice. In certain patients, veins of adequate diameter to accept two leads may be a limiting factor. Generally, insertion of a pervenous lead for short-term use is accomplished under conditions where time is an important factor. Endocardial pacing or mapping accuracy, speed and efficiency are typically quite difficult to achieve when utilizing two separate leads for multiple functioning or when even using a single lead provided with multiple functioning stations which are generally stationarily fixed relative to one another thereby making it difficult to modify the mapping surface or pacing electrode locations.

The size and configuration of hearts may vary somewhat substantially, and difficulty has been encountered in achieving and maintaining reliable contact with the atrial muscle during endocardial procedures. The surfaces being paced or mapped usually will be concave or generally flat, but unless the electrodes of the pacing or mapping assemblies exhibit some degree of adjustability, it is not possible to have the same device pace or map such a variety of surface configurations. This type of adjustability is rendered more difficult when such must be provided for in an endocardial device which, ideally, should be isodiametric throughout the length of the device. Various curves along the length of the lead or the addition of various appendages to the lead may cause difficulties not only during endocardial insertion but also during removal attempts.

Accordingly, there is a need for a multiple functioning percutaneous lead to achieve endocardial pacing, mapping and other procedures which may be readily inserted and removed under conditions where time is an important factor, and which is capable of establishing and maintaining reliable contact with the portions of the heart undergoing testing and/or treatment. A general object of the present invention is to provide such a lead which exhibits adjustability between isodiametric and outwardly extending electrode configurations.

Another object of this invention is to provide an improved percutaneous lead that functions in the manner of an endocardial catheter that can be guided through a narrow body passageway such as a vein or an artery when it has a substantially isodiametric configuration, but which can, after it has been properly positioned within the body, be manipulated such that distal electrodes are movable outwardly therefrom to establish effective ventricular and atrial surface contact in hearts of variable size and configuration, thus providing effective mapping and/or pacing functions.

Still another object of the present invention is to provide a readily insertable and removable ventricular-/atrial pervenous lead for cardiac pacing or diagnosis which is relatively inexpensive and disposable and which, in its pervenous advanceable and retractable condition, is isodiametric.

An additional object of the present invention is to provide an adjustable isodiametric atrial-ventricular pervenous lead of the type described which is readily manipulated externally of the body to independently adjustably place multiple electrode assemblies in effective contact with surfaces of the heart undergoing diagnosis and/or treatment.

SUMMARY OF THE INVENTION

The invention is directed to a combined ventricular-/atrial pervenous lead for cardiac pacing or diagnosis, the lead including an elongated tube-like member having longitudinally spaced ventricular and atrial electrode assemblies established to function independently, both mechanically and electrically, as well as function cooperatively in response to external control. The lead is isodiametric in its pervenous advanceable condition, the ventricular electrode assembly being advanceable and retractable at the distal end of the lead while the atrial electrode assembly is longitudinally spaced from the ventricular electrode assembly and the distal end of the lead, and the atrial electrode is radially expandable relative to the longitudinal axis of the lead for adjustable engagement with atrial muscles of variable configurations. The tube-like member of the lead is interrupted along its length to contain the atrial electrode assembly, and a portion thereof is movable by external manipulation relative to another portion thereof to provide for controlled radial expansion or extension of the atrial electrode assembly.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a schematic illustration of a heart in cross section showing the operational insertion of the lead of the present invention therein;

FIG. 2 is a longitudinal partial cross-sectional, partly fragmented view of the preferred embodiment of the lead of the present invention;

FIG. 3 is a fragmented top plan view of a portion of the lead as viewed along line 3—3 of FIG. 2;

FIG. 4 is a fragmented elevational view of the lead of FIG. 2, shown in its isodiametric configuration;

FIG. 5 is a fragmented elevational view of the lead of FIG. 2, shown with the atrial electrode and the ventricular electrode in respective extended or operational orientations thereof;

FIG. 6 is a fragmented elevational view of a modified form of a lead according to the present invention, shown in its isodiametric configuration; and FIG. 7 is an elevational fragmented view of the modified lead of FIG. 6, illustrating the extended or operational orientation thereof.

DESCRIPTION OF THE PREFERRED EMBODIMENTS

FIG. 1 illustrates schematically the human heart 10 having a ventricle 11 and an atrium 12, the atrial muscle or wall surface being identified by the numeral 13. An isodiametric, pervenous, adjustable atrial-ventricular lead, generally designated as 14, is illustrated as being operatively inserted in the heart 10 with an extended ventricular electrode assembly, generally designated as 15, projecting from the distal end of the lead in operative engagement with a wall surface of the ventricle 11. Longitudinally spaced from the ventricular electrode assembly 15, the lead is provided with a radially expandable atrial electrode assembly, generally designated as 16, having an operative portion thereof in engagement with the atrial muscle 13. The proximal end of the lead 14, which would be located externally of the body of the patient, is provided with manipulative control members constituting a control assembly 17. This control assembly is operable to independently extend and retract the ventricular electrode assembly 15 at the distal end of the lead, as well as independently radially extend and retract the atrial electrode assembly 16 located longitudinally inwardly from the distal end of the lead 14.

As best illustrate in FIG. 4, the lead 14 in its pervenously advanceable and retractable conditions is isodiametric thereby readily assisting insertion into and withdrawal from the veins and from the heart while retaining the multiple mapping and treatment functions to be described. Referring in particular to FIG. 2, the lead 14 includes an outer sheath which constitutes an elongated outer housing which is in the form of a tube and which is divided into a pair of first and second tube members 18 and 19, respectively. The ventricular electrode assembly 15 extends from the first tube member 18 and is substantially adjacent the distal end thereof, while the atrial electrode assembly 16 is longitudinally spaced from the ventricular assembly 15 and is located between the proximal end of the first tube member 18 and the distal end of the second tube member 19. The control assembly 17 is located adjacent the proximal end of the second tube member 19. This proximal end of the second tube member 19 is provided with an enlarged annular flange 20 which may be considered to form a part of the control assembly 17 but which, at any rate, is designed to be grasped by the user during adjustment of the lead as will be described.

Within the longitudinally extending sheath defined by the first and second tube members 18 and 19, an elongated inner tube member 21 is provided. The lumen 22 of each of the tube members 18 and 19 is of the same dimension and readily receives the inner tube member 21 therein. The inner tube member 21 projects just inwardly of the proximal end of the first tube member 18, extends the full longitudinal length of the second tube member 19 and projects outwardly from the proximal end of the second tube member 19. The outwardly projecting end of the inner tube member 21 is provided with an annular flange 23 which forms a part of the control assembly 17 and is manipulated as will be described.

The ventricular electrode assembly 15 consists of an electrode 24 of suitable configuration such as the illustrated semi-spherical configuration which, in the unextended condition of the lead, abuts the distal end of the first tube member 18, as best illustrated in FIG. 4. A longitudinally extending electrode conductor/extender 25 is connected in electrical communication with the electrode 24 in a suitable manner, not shown. The conductor/extender 25 is received through the lumen 22 of the tube members 18 and 19 as well as the lumen 26 of the inner tube member 21, the diameter of the conductor/extender being such as to permit ready longitudinal movement thereof relative to the various tube members. The proximal end of the conductor/extender 25 projects from the proximal end of the inner tube 21 and is provided with a suitable button or flange 27 which forms a part of the control assembly 17 for manipulation of the conductor/extender to advance or retract the ventricular electrode assembly 15.

A plunger-like sheath 28 of cylindrical configuration is formed about the distal end of the conductor/extender 25 adjacent the ventricular electrode 24. The sheath 28 is provided with a proximal cylindrical flange 29 received within the first tube member 18 which limits the extent of distal-direction advancement of the ventricular electrode assembly 15 with respect to the distal end of the tube member 18. Included in this regard is an internal end cap 30 of annular configuration received within the distal end of the first tube member 18 and provided with a central aperture 31 through which the sheath 28 moves. The aperture 31 is dimensioned to sufficiently engage the sheath 28 to seal the first tube member at the distal end thereof from ingress of fluid while the ventricular electrode assembly 15 is being manipulated. The flange 29 of the sheath 28 will abut the inner radial surface of the end cap 30 at the position of fullest extension of the ventricular electrode assembly 15 from the distal end of the first tube member 18, thus limiting total extension.

The ventricular electrode 24 may be formed from stainless steel or other suitable electrode material, with the conductor/extender wire 25 being formed of stainless steel or other suitable conductive and stiff material and suitably welded to the electrode 24. The sheath 28 may be formed from a biocompatible polymer or resin such as a polyurethane, with the conductor/extender wire 25 suitably extending therethrough. Both of the tube members 18 and 19 as well as the inner tube member 21 may also be formed from a suitable biocompatible polymer or resin such as a polyurethane. These materials are selected as being biocompatible while being sufficiently longitudinally rigid and transversely bendable for efficient pervenous insertion and retraction.

Still referring primarily to FIG. 2, the atrial electrode assembly 16 includes an outer flexible sheath 32 which is tubular in configuration to generally conform with the shape of the tube members 18 and 19. Sheath 32, which extends between the adjacent ends of the tube members 18 and 19 to basically define the outer configuration of the lead, may be formed of a material that is flexible such as a silastic material. Opposite ends of the sheath 32 are suitably bonded to adjacent ends of the tube members 18 and 19, and a first bushing or connecting means 33 is located at the proximal end of the tube member 18 and at the distal end of the inner tube member 21. Connecting means or bushing 33 also overlaps the bonded adjacent area of the sheath 32. The bushing 33 is suitably crimped or bonded to the distal end of the inner tube member 21. The outer surface of the bushing 33 is also suitably bonded to the sheath 32 which, in turn, is bonded to the proximal end of the outer tube member 18. In this manner the bushing 33 fixes the inner tube member 21 to the outer tube member 18 so as to prevent relative movement therebetween.

As previously stated, the proximal end of the flexible sheath 32 is bonded to the distal end of the second tube member 19. Overlapping this area of bonding is a second bushing or connecting means 34 which along at least a portion of the outer diameter thereof is also bonded to the flexible sheath 32. The inner diameter of the bushing 34 includes a lumen 35 which establishes a longitudinal clearance or slidability between the inner diameter of the bushing 34 and the outer diameter of the inner tube member 21. By reason of this lumen, relative longitudinal movement between bushing 34 and the inner tube member 21 can occur for a purpose to be described.

The outer surface of the bushing 34 also has attached thereto a longitudinally extending atrial electrode 36 which is fastened at its opposite end to the outer surface of the bushing 33. As best seen in FIG. 3, the electrode 36 is a thin flat wire, the wire being substantially contiguous with the sheath 32. The sheath 32 in the area of the extension of the atrial electrode 36 is slotted at 37 to expose a substantial portion of the electrode 36. An electrode lead 38 is attached to the bushing 34 and extends in the lumen 22 of the tube member 19 outwardly of the proximal end thereof for suitable connection to the atrial terminal of an external cardiac pacer or analyzer (not shown). Similarly, the conductor/extender 25 of the ventricular electrode assembly 15 is provided with a flexible connector (not shown) for connection in a known manner to an external cardiac pacer or analyzer. In this manner suitable power is applied to both the ventricular and atrial electrode assemblies for operation thereof in diagnosing and/or pacing the heart. The bushings 33 and 34 as well as the lead 38 may be formed from stainless steel or other suitable conductor.

As best seen in FIG. 3, the atrial electrode assembly sheathing 32 is provided with oppositely positioned notches 39 adjacent the center point of the atrial electrode 36, which notches 39 may be contiguous with the slot 37. The notches 39 facilitate radially outwardly directed flexing of the sheath 32 during positioning of the atrial electrode assembly 16 as will now be described.

FIG. 5 illustrates the manipulative use of the lead 14 after same is introduced into the heart 10 as schematically illustrated in FIG. 1. During pervenous insertion of the lead 14, the same is manipulated in isodiametric condition as illustrated in FIG. 4. This isodiametric condition, when combined with the multiple capabilities of the lead in diagnosis and treatment, greatly enhances its functional utilization and speed of utilization while eliminating the more intrusive epicardial approach. For example, subcutaneous introduction of the lead into a vein results in advancement of the lead to the right ventricle and right atrium of the heart of a cardiac patient. Advancement through an artery would be needed for placement in the left ventricle. During such advancement procedure, the lead 14 will remain in its isodiametric configuration, such as that illustrated in FIG. 4, and gross positioning of the lead 14 to near the desired site is accomplished, typically aided by fluoroscopy. Fine positioning of the lead is aided by sensing the electrical potential at each electrode 24 and 36, using one or the other as a reference.

Fine positioning of the lead results from manipulative use of the control assembly 17 in association with information obtained from the external cardiac unit (not shown). The ventricular electrode 24 is advanced beyond the distal end of the first tube member 18 into the ventricular cavity 11 of the heart by forward movement of the knob 27 attached to the conductor/extender 25. As previously described, the ventricular electrode assembly moves freely within the lumen 26 of the inner tube member 21. Fine positioning of the atrial electrode assembly 16 results from relative movement of the flanges 20 and 23 of the control assembly 17, such movement normally consisting of holding the flange 23 against movement and pressing the flange 20 forwardly to move the second tube member 19 toward the first tube member 18 relative to the inner tube member 21. The bushing 34 will move forwardly with the second tube member 19 causing the atrial electrode 36 and sheath 32 to arch or expand radially outwardly as illustrated in FIG. 5. In this manner, the electrode 36 may be brought into contact with the atrial wall surface 13 for positioning the lead for atrial pacing and/or mapping and the like.

While the foregoing particular mode of adjustment of the lead within the heart has been described, it will be understood that a reverse procedure may be utilized. For example, the flange 23 of the inner tube member 21 may be moved outwardly from the flange 20 of the outer tube 19 thus retracting the tube member 18 toward the tube member 19 and causing the atrial electrode 37 and sheathing 32 to bow radially outwardly as previously described. If the ventricular electrode 24 has already been finely positioned, such position is not disturbed because lumen 26 permits movement of the inner tube member 21 relative to the conductor/extender 25 up until the flange 29 engages the end cap 30. Thus, complete versatility is obtained by reason of the particular design described.

Once the electrodes have been desirably located and positioned, prevention of displacement of the two electrodes 24 and 36 may be accomplsihed, if desired, by locking the leads in place proximally of the unit. Such may be accomplished, for example, by the placement of medical adhesive or the like beween the respective proximal portions of inner and outer tube members or by the placement of a suture around these tube members or the control means therefor, and anchoring the suture through the skin.

The notches 39 of the sheath 32 of the atrial electrode assembly 16 assist in causing the sheath 32 to arch or bow outwardly as described. Preferably, the atrial electrode 36 is suitably insulated along the inner surface thereof. This precisely defines the effective area of the electrode. In one form of the invention, the sheath 32 of the atrial electrode assembly may form an arc of about 200 degrees. The metallic nature of the electrode 36 permits it to function much like a spring thus assisting in returning the atrial electrode assembly to its isodiametric condition when the lead is to be withdrawn. If desired, an additional atrial electrode 36 may be provided at approximately 180 degrees relative to the first electrode thus allowing bipolar pacing and sensing in the atrium. The structure of the lead described would also permit, for example, the use of three such electrodes placed in an equilateral triangular arrangement.

FIGS. 6 and 7 illustrate a further embodiment of the lead of the subject invention. All of the parts described hereinabove remain the same except that multiple electrodes are provided in the atrial electrode assembly, this modified atrial electrode assembly being identified generally by the reference numeral 40. In this modified assembly 40, the sheath 32 is provided with a plurality of longitudinal slits 41 which define circumferentially spaced ribbon portions 42 of the silastic material, each ribbon portion 42 bowing outwardly when the lead is manipulated as described above. In the embodiment shown in FIGS. 6 and 7, four such ribbon portions 42 are illustrated.

Each ribbon poriton 42 is provided with a flexible atrial electrode 43 attached at its proximal end to the previously described bushing 34. Multiple external flexible leads, such as the type of lead 38 previously described, ar suitably connected to the electrodes 43 and extend from the proximal end of the tube member 19 for connection with an external cardiac unit (now shown). The distal ends 44 of the electrodes 43 are received through suitable apertures in the ribbons 42 and extend sufficiently along the outer surfaces of the ribbons in suitable attachment therewith for contact with surfaces of the heart. A reasonable number of such independent electrodes 43 may be used, the number illustrated being four which is considered feasible. This modified lead will operate in the same manner as described above, with movement of the outer tube member 19 relative to the inner tube member 21 causing the ribbons 42 of the sheath 32 to arch radially outwardly, each ribbon carrying its electrode end 44 in an exposed manner so as to be useful in contacting various surface areas in the atrium for diagnosis and treatment.

As can be appreciated, the ventricular electrode assembly may be advanced to any desired length up to its maximum length. Similarly, the atrial electrode assembly may be expanded to any degree of arch up to its maximum expansion. Thus, the distance between the ventricular and atrial electrodes is adjustable to match the specific anatomy of the heart of a patient. The isodiametric feature of the lead permits single passing of both the ventricular and atrial electrodes through a common vein using a single sheath introducer. The lead may also be removed in an isodiametric fashion when it is no longer needed. Any aggregate substance, such as a clot, fibrin, and the like, may be removed with the lead as it will be trapped within the interior of the atrial electrode assembly when the same is returned to its previously flat condition. Upon removal of the lead, it will not be necessary to return the ventricular electrode assembly to its original position because this assembly retains the desired isodiametric configuration of the lead even while extended.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A ventricular/atrial pervenous lead for cardiac pacing or diagnosis, comprising:
    an elongated outer housing having a proximal end and a distal end and further including longitudinally spaced ventricular and atrial electrode assemblies, said elongated outer housing being substantially isodiametric with said atrial electrode assembly in its pervenous advanceable condition; and
    longitudinally extending movable means for independently advancing said ventricular electrode assembly relative to said housing and for independently generally radially expanding said atrial electrode assembly relative to said housing.

2. The lead according to claim 1, wherein said movable means includes a plurality of portions of said elongated outer housing, one of said portions being movable relative to another of said portions for independently expanding said atrial electrode assembly.

3. The lead according to claim 2, wherein said ventricular electrode assembly is positioned at the distal end of said housing, and said atrial electrode assembly is positioned longitudinally inwardly of said distal end; and
    control means are located at the proximal end of said housing for operating said movable means.

4. The lead according to claim 1, wherein said ventricular electrode assembly is positioned at the distal end of said housing, and said atrial electrode assembly is positioned longitudinally inwardly of said distal end.

5. The lead according to claim 4 wherein said movable means includes a plurality of portions of said elongated outer housing, one of said portions being movable relative to another of said portions for independently expanding said atrial electrode assembly.

6. The lead according to claim 1, wherein control meeans are provided at the proximal end of said housing to operate said movable means.

7. The lead according to claim 6, wherein said movable means includes a plurality of portions of said elongated outer housing, one of said portions being movable relative to another of said portions for independently expanding said atrial electrode assembly.

8. The lead according to claim 1, wherein said atrial electrode assembly includes a flexible sheath having at least one electrode exposed therethrough.

9. The lead according to claim 1, wherein said atrial electrode assembly includes a flexible sheath having at least one electrode exposed therethrough, and connecting means is provided for connecting said sheath to the proximal end of said elongated outer housing.

10. A ventricular/atrial pervenous lead for cardiac pacing or diagnosis, comprising:
  a pair of normally spaced first and second outer tubular members, said first and second outer tubular members each having a distal end and a proximal end;
  a radially outwardly movable flexible atrial electrode assembly interconnecting said proximal end of the first outer tubular member and said distal end of the second outer tubular member;
  an inner tubular member extending through said first and second outer tubular members and through said atiral electrode assembly, said inner tubular member having a distal end;
  a ventricular electrode assembly extending through and projecting from the distal end of the first of said outer tubular members and the distal end of said inner tubular member, said ventricular electrode assembly having a distal portion;
  first connecting means fixing said first of said outer tubular members and said inner tubular member against relative longitudinal movement; and
  second connecting means interconnecting the second of said outer tubular members to said atrial electrode assembly for movement of said second outer tubular member relative to said inner tubular member and for radially outwardly flexing said atrial electrode assembly.

11. The pervenous lead according to claim 10, wherein said first connecting means is located at the proximal end of said first outer tubular member and the distal end of said inner tubular member.

12. The pervenous lead according to claim 11, wherein said atrial electrode assembly includes a flexible sheath having at least one electrode exposed therethrough, and said first connecting means is for connecting said sheath to the proximal end of said first outer tubular member.

13. The pervenous lead according to claim 12, wherein the distal end of said first outer tubular member and the distal portion of said ventricular electrode assembly extending therethrough include sealing means for preventing the ingress of fluid into said first outer tubular member.

14. The pervenous lead according to claim 13, wherein said ventricular electrode assembly includes a conductor/extender extending through said inner tubular member and exposed at the proximal end of the second of said outer tubular members.

15. The pervenous lead according to claim 10, wherein the distal end of said first outer tubular member and the distal portion of said ventricular electrode assembly extending therethrough include sealing means for preventing the ingress of fluid into said first outer tubular member.

16. The pervenous lead according to claim 10, wherein said first and second outer tubular members are substantially isodiametric with said flexible atrial electrode assembly in its pervenous advanceable condition.

17. The pervenous lead according to claim 10, wherein said ventricular electrode assembly includes a conductor/extender extending through said inner tubular member and exposed at the proximal end of the second of said outer tubular members.

18. The pervenous lead according to claim 10, wherein said atrial electrode assembly includes a flexible sheath having at least one electrode exposed therethrough.

* * * * *

UNITED STATES PATENT AND TRADEMARK OFFICE
CERTIFICATE OF CORRECTION

PATENT NO. : 4,664,120

DATED : May 12, 1987

INVENTOR(S) : Stanley R. Hess

It is certified that error appears in the above-identified patent and that said Letters Patent are hereby corrected as shown below:

Column 7, line 10, "accomplsihed" should read --accomplished--; line 52, "ar" should read --are--; line 54, "(now shown)" should read --(not shown)--.

Signed and Sealed this

Twenty-fourth Day of November, 1987

Attest:

DONALD J. QUIGG

*Attesting Officer*  *Commissioner of Patents and Trademarks*